United States Patent [19]

Azam

[11] 4,192,998
[45] Mar. 11, 1980

[54] NEUTRONTHERAPY APPARATUS USING A LINEAR ACCELERATOR OF ELECTRONS

[75] Inventor: Guy Azam, Paris, France

[73] Assignee: C.G.R.-MeV, Buc, France

[21] Appl. No.: 875,576

[22] Filed: Feb. 6, 1978

[30] Foreign Application Priority Data

Feb. 8, 1977 [FR] France .................. 77 03478

[51] Int. Cl.² .......................................... G21G 4/02
[52] U.S. Cl. .............................. 250/502; 250/499; 250/515; 250/518
[58] Field of Search ........................ 250/505, 499-, 250/502, 518, 515

[56] References Cited

U.S. PATENT DOCUMENTS

| | | | |
|---|---|---|---|
| 3,781,564 | 12/1973 | Lundberg | 250/505 |
| 3,963,934 | 6/1976 | Ormrod | 250/499 |
| 3,995,163 | 11/1976 | Colditz | 250/515 |

Primary Examiner—Harold A. Dixon
Attorney, Agent, or Firm—Cushman, Darby & Cushman

[57] ABSTRACT

Neutron-based radiotherapy apparatus comprising a linear charged-particle accelerator which delivers a beam of accelerated electrons, a target intended to be bombarded by the beam of accelerated electrons for emitting neutrons under the impact of that beam, means for cooling the target, means for eliminating parasitic radiations, and a collimation system for the useful beam of neutrons. The electron accelerator may be arranged either on the inside or on the outside of the rotating arm of the neutron-radiotherapy apparatus.

7 Claims, 4 Drawing Figures

NEUTRONTHERAPY APPARATUS USING A LINEAR ACCELERATOR OF ELECTRONS

FIELD OF THE INVENTION

The present invention relates to a neutrontherapy apparatus in which the beam of neutrons is obtained by bombardment of a target by an accelerated electron beam.

DISCUSSION OF THE PRIOR ART

The irradiation apparatus and more particularly the radiotherapy apparatus use, either radiation beams furnished by radioactive sources (gammatherapy), or accelerated charged particle beams, or beams of X-rays obtained by the bombardment of a target of a suitably selected material by a beam of accelerated particles. It is also known to use neutron beams for specific medical traitments, these neutron beams being obtained by bombardment of targets of low Z with accelerated positive ions, and the neutrons being produced by $^3H (d, n)^4 He$ reaction (often referred to as D-T reaction). However, the neutron-radiotherapy apparatus are cumbersome and heavy and moreover presents technical problems, in particular the target-to-skin distances which must be in excess to 100 cm.

It is the primary object of the invention to provide a neutrontherapy apparatus of relatively weak cumbersome and for which the above mentioned drawbacks are eliminated.

SUMMARY OF THE INVENTION

According to the invention, a neutrontherapy apparatus delivering a neutron beam by bombardment of a metal target by means of an accelerated electron beam, comprising an accelerator for accelerating electrons emitted by an electron source, a target intended to be bombarded by the beam of accelerated electrons for emitting neutrons under the impact of said electron beam, means for cooling the target, means for eliminating the parasitic radiations produced by the bombardment of the target by said beam of accelerated electrons, a system for collimating the useful beam of neutrons and means for controlling the characteristics of the useful beam of neutrons.

BRIEF DESCRIPTION OF THE DRAWINGS

For a better understanding of the invention and to show how the same may be carried into effect, reference will be made to the drawings, given solely by way of example which accompagny the following description, and wherein.

DETAILED DESCRIPTION

Figure 1:
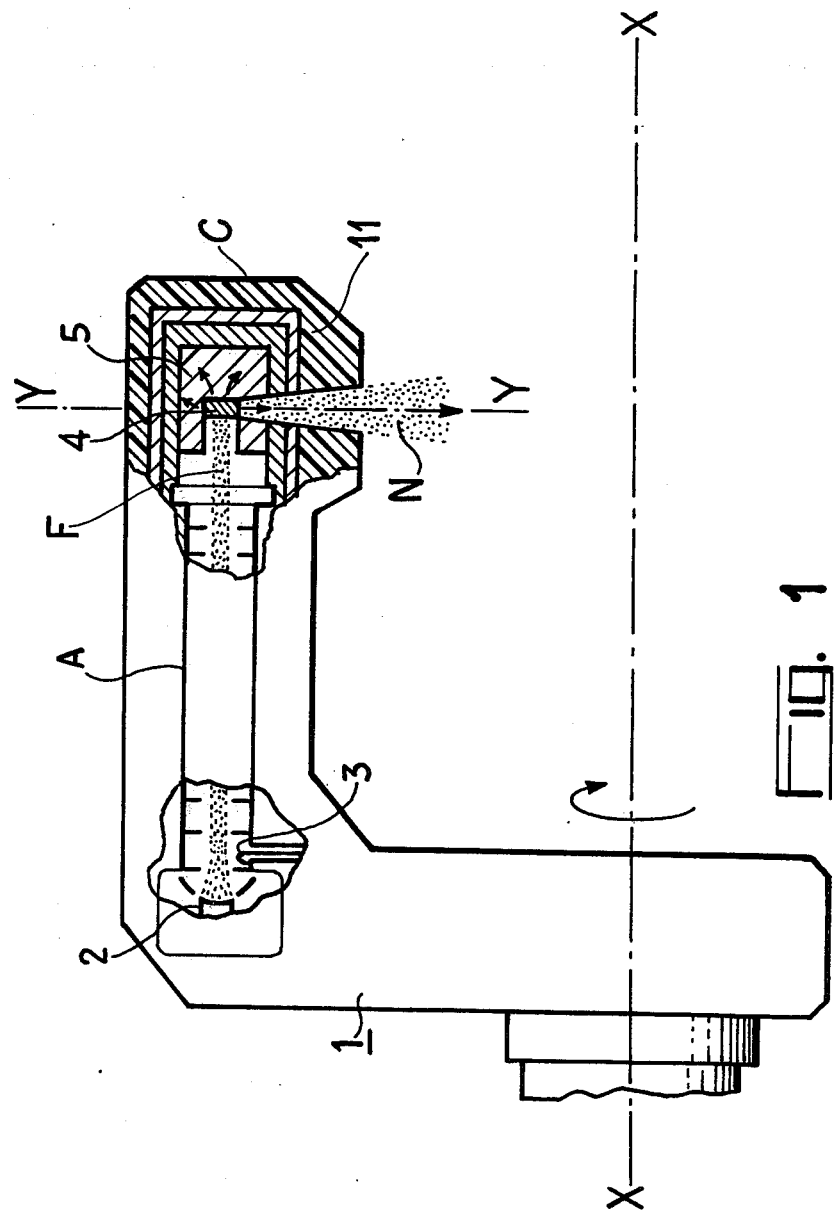
FIG. 1 diagrammatically illustrates one example of embodiment of a neutrontherapy apparatus according to the invention.

The neutrontherapy apparatus according to the invention, such as illustrated in FIG. 1, comprises a moving arm 1 which is capable of turning through 360° about a horizontal axis XX.

Figure 2:
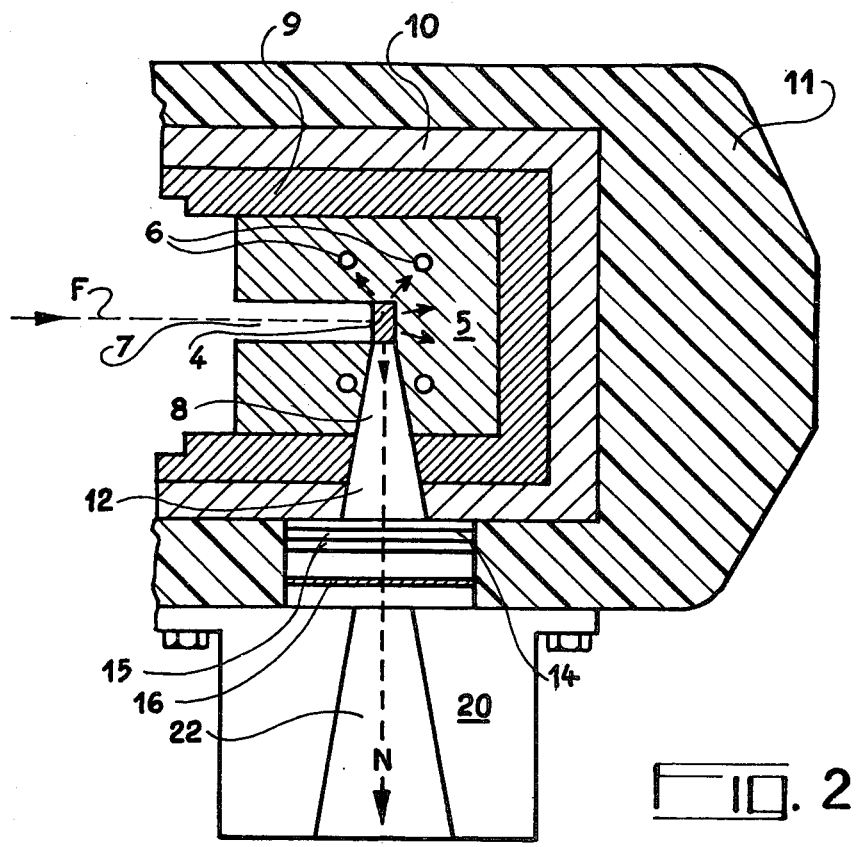
FIG. 2 shows an irradiation head of a neutrontherapy apparatus according to the invention.

Accommodated in this moving arm 1 is a linear particle accelerator A which accelerates the electrons of a beam F of electrons coming from a source 2. A coupling system 3 enables a high-frequency signal to be injected into the accelerator A. At the output end of the accelerator A there is a target 4 located in a first block 5 of copper provided with a cooling system, having the form of tubes 6 for example, through which a cooling fluid is capable of circulating. As shown in FIG. 2, this block 5 is provided with a first passageway 7 for the passage of the beam F of accelerated electrons and with a second passageway 8 for the passage of the useful beam N of neutrons. In the embodiment shown in FIG. 2, the passageway 8 is arranged at an angle of 90° relative to the passageway 7 which readily enables the parasitic photons emitted by the target 4 in the direction of the electron beam F to be eliminated. The block 5 is surrounded by a protective shield 9 which itself is surrounded by a shield 10, the shields 9 and 10 together being intended to stop the flux of parasitic photons. In the described embodiment, the shields 9 and 10, made respectively of tungsten and lead, are disposed in a protective block 11 made of a material of high hydrogen content, for example polyethylene (or wood treated with boron or even water), which absorbs the neutrons emitted by the target 4 (isotropic emission) except for the useful flux of neutrons travelling through the passageway 12 provided for this purpose. The assembly formed by the target 4 and its protective elements (shields 9, 10 and protective block 11) is accommodated in the irradiation head of the neutrontherapy apparatus according to the invention. At the exit zone of the irradiation head in the path followed by the useful beam N of neutrons, there are successively disposed, on the one hand, a measuring chamber 14 containing a system 15 for monitoring the alignment, homogeneity and irradiation dose of the useful beam N of neutrons, an equalising filter 16 and, on the other hand, a collimator 20. This measuring system 15, is associated with a safety device (not shown in the FIGS.) which controls the operation of the electron accelerator A.

Figure 3:
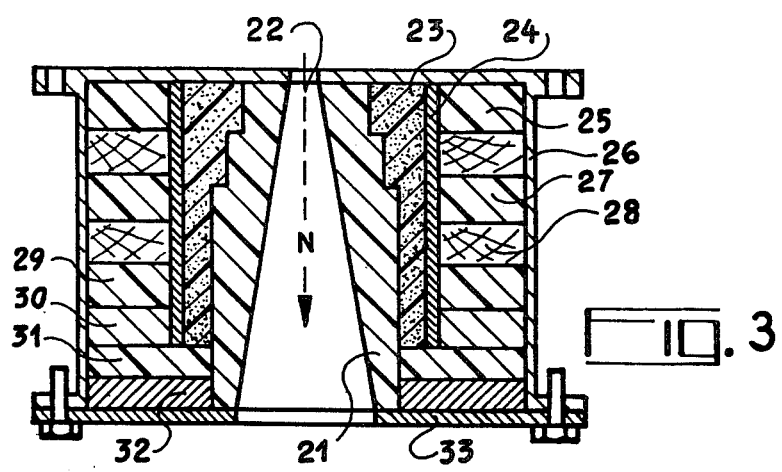
FIG. 3 shows a collimator used in a neutrontherapy apparatus according to the invention.

FIG. 3 shows one example of embodiment of a collimator used in a neutrontherapy apparatus according to the invention. This collimator 20 is formed by a removable block 21 of polyethylene of which the passageway 22, intended for the passage of the useful beam N of neutrons, is of predetermined dimensions. The block 21 is surrounded by an assembly of protective elements 23 to 33 made either of a homogeneous material (elements 24, 30, 32, 33 for example) or of a composite material (element 23 made of polyethylene and tungsten powder for example). In the embodiment shown in FIG. 3, the element 24 is made of lead, the elements 25, 27, 29 of polyethylene and boron, the elements 26 and 28 of wood treated with boron, the element 30 of steel, the element 32 of tungsten and, finally, the element 33 of lead. The arrangement of these various elements 23 to 33 and also their composition have been given purely by way of example.

In operation, the beam of accelerated electrons coming from the accelerator A (FIG. 1) strikes the target 4 without preliminary deviation. Some of the neutrons emitted isotropically by the target 4 pass through the passageways 8 and 22 (FIG. 2) which delimit the useful beam N of neutrons travelling in a direction YY perpendicular to the mean path of the beam F of accelerated electrons. The density of photons along this axis YY (which is orthogonal to the principle emission lobe of the photons) is very low which enables a useful beam N of suitable purity to be obtained.

By way of non-limiting example, a neutrontherapy apparatus according to the invention of the type described above, using a linear accelerator supplying a beam of electrons of about 15 MeV by the bombardment of a tungsten target, is capable of supplying a beam of neutrons of 2 to 7 MeV, the electron/neutron conversion efficiency being of the order of $2.10^{-4}$ neutrons per electron and per MeV.

Figure 4:
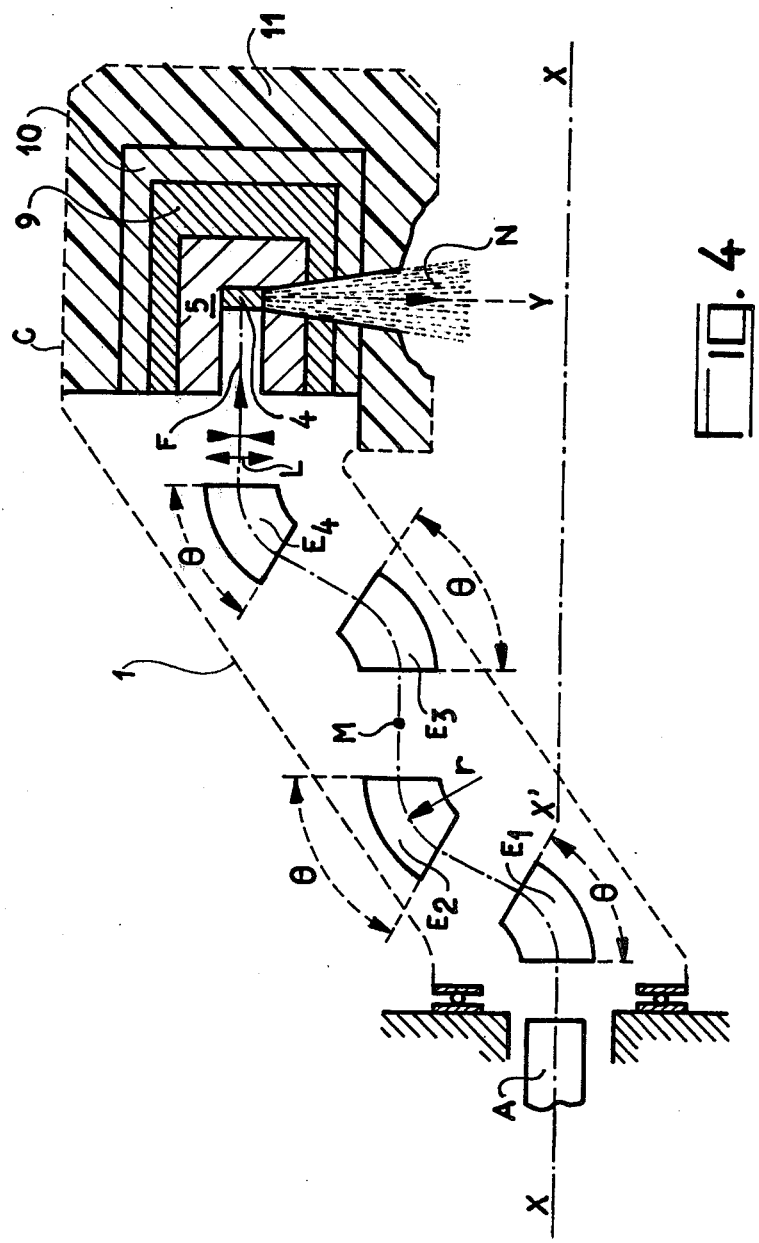
FIG. 4 shows another example of embodiment of a neutrontherapy apparatus according to the invention.

If the treatment requires a beam N of neutrons of greater intensity and energy, corresponding to a beam F of accelerated electrons of 25 to 30 MeV for example, it is possible to use a variant of the neutrontherapy apparatus according to the invention described above. In this variant, which is shown in FIG. 4, the electron accelerator A is arranged outside the rotating arm 1 having a rotating axis XX which is coincidental with the mean path of the beam F of accelerated electrons issued from the linear accelerator A, the mean path being translated in a direction perpendicular to the axis XX. This translation may be obtained by means of a translation system such as described by the French Patent No. 70 02 468 for example. This translation system, shown diagrammatically in the neutrontherapy apparatus of FIG. 4, is stigmatic and achromatic. It consists of four electromagnets $E_1$, $E_2$, $E_3$, $E_4$ generating magnetic fields running parallel to one another and perpendicular to the planes of symmetry of the air gaps of the electromagnets (plane of FIG. 4). The arrangement of the electromagnets $E_1$ to $E_4$ is such that their centre of symmetry is a point M which coincides with the focal point of the particle quantum. The distance L between the opposite faces of two successive electromagnets is equal to $L=2r/\text{tg}\,\theta$, r being the radius of curvature of the mean path of the beam of electrons in the electromagnets $E_1$ to $E_4$ and $\theta$ being the angle which the entry and exit faces of each of the electromagnets $E_1$ to $E_4$ form with one another. The entry face of the electromagnet $E_1$ is perpendicular to the mean path of the beam of electrons coming from the accelerator A (axis XX), whilst the exit face of the electromagnet $E_4$ is perpendicular to the emerging beam. In the example of embodiment which has just been described, the translation which the beam of electrons undergoes will be substantially equal to $l=4r$. A magnetic lens L may be arranged at the exit of the translation system in order suitably to focus the beam F of accelerated electrons on the target 4.

What I claim is:

1. A neutrontherapy apparatus comprising a linear accelerator for accelerating electrons emitted by an electron source, a target intended to be bombarded by said beam of accelerated electrons for emitting neutrons under the impact of said accelerated electron beam, means for cooling said target, means for eliminating the parasitic radiations produced by the bombardment of said target, a collimation system for the useful beam of neutrons and control means for controlling the characteristics of the useful beam of neutrons, the useful beam of neutrons and control means for controlling the characteristics of the useful beam of neutrons, said target being accommodated in a block of a highly heat-conductive material, said block being provided with a circulation system for a cooling fluid, said block comprising a first passageway for the passage of said accelerated electron beam and a second passageway for the passage of said useful beam of neutrons, said block being arranged inside an assembly of protective shields which are capable of stopping the parasitic photons and which are accommodated in a protective block capable of arresting the parasitic neutrons, said protective block being made of a material of high hydrogen content, said shields and said protective block being provided with orifices providing respectively for the passage of the beam of accelerated electrons and the passage of the useful beam of neutrons.

2. A neutrontherapy apparatus as claimed in claim 1, wherein said target is made of tungsten.

3. A neutrontherapy apparatus as claimed in claim 1, wherein said shields, nesting in one another, are two in number, the first being made of tungsten and the second of lead.

4. A neutrontherapy apparatus as claimed in claim 1, wherein said control means comprise a measuring chamber arranged in the path of the useful beam of neutrons in the exit zone of said protective block, said measuring chamber comprising a system for monitoring the positioning, homogeneity and irradiation dose of the useful beam of neutrons, an equalising filter, and a safety device which is associated with said monitoring systems which control the operation of the electron accelerator.

5. A neutrontherapy apparatus as claimed in claim 1, wherein said collimation system comprises a first element 21 of polyethylene formed with a central opening (22) for the passage of the useful beam N of neutrons, a second element 23 of a composite material of polyethylene and tungsten, a sleeve (24) of lead surrounding the two elements (21, 23) and an assembly of elements (25 to 32) forming a laminated protection block of cylindrical shape of which the axis YY of revolution coincides with the mean path of the useful beam N of neutrons.

6. A neutrontherapy apparatus as claimed in claim 2, comprising a rotating arm with an irradiation head arranged at its free end, said electron linear accelerator being accommodated in said rotating arm and said target and said blocks and protective shields which are associated with it being accommodated in said irradiation head, 7. A neutrontherapy apparatus as claimed in claim 1, comprising a rotating irradiation arm having an axis XX of rotation, said electron linear accelerator being arranged outside said rotating arm along the axis of rotation XX of the rotating arm, a stigmatic and achromatic translation system for translating the beam of accelerated electrons being accommodated in the rotating arm in such a way that the electron beam emerging from the translation system is parallel to the axis XX and perpendicular to said target, the mean path of the useful beam N of neutrons being perpendicular to said axis XX.

* * * * *